United States Patent
Huang

(10) Patent No.: US 10,803,993 B2
(45) Date of Patent: Oct. 13, 2020

(54) PROXIMITY TRACING METHODS AND SYSTEMS

(71) Applicant: Stuart Tin Fah Huang, Honolulu, HI (US)

(72) Inventor: Stuart Tin Fah Huang, Honolulu, HI (US)

(*) Notice: Subject to any disclaimer, the term of this patent is extended or adjusted under 35 U.S.C. 154(b) by 386 days.

(21) Appl. No.: 15/405,321

(22) Filed: Jan. 13, 2017

(65) Prior Publication Data

US 2017/0206334 A1 Jul. 20, 2017

Related U.S. Application Data

(60) Provisional application No. 62/278,983, filed on Jan. 14, 2016, provisional application No. 62/364,193, filed on Jul. 19, 2016.

(51) Int. Cl.
G16H 50/30 (2018.01)

(52) U.S. Cl.
CPC ................... *G16H 50/30* (2018.01)

(58) Field of Classification Search
CPC ........ G16H 50/30; G16H 50/80; G16H 50/20; G16H 50/70
USPC ............................................. 705/2
See application file for complete search history.

(56) References Cited

U.S. PATENT DOCUMENTS

| | | |
|---|---|---|
| 2003/0204130 A1 | 10/2003 | Colston, Jr. et al. |
| 2006/0220879 A1 | 10/2006 | Chan |
| 2009/0070134 A1* | 3/2009 | Rodgers .......... G06Q 50/22 705/2 |
| 2010/0097209 A1 | 4/2010 | Wong |
| 2010/0112883 A1 | 5/2010 | Wallace et al. |
| 2011/0093249 A1* | 4/2011 | Holmes ............ G06F 19/00 703/6 |
| 2012/0112883 A1 | 5/2012 | Wallace et al. |
| 2013/0318027 A1 | 11/2013 | Amogy et al. |
| 2014/0167917 A2 | 6/2014 | Wallace et al. |

OTHER PUBLICATIONS

International Searching Authority, Notification of Transmittal of the International Search Report and the Written Opinion of the International Searching Authority, or the Declaration, International application No. PCT/US17/13380, dated Jun. 26, 2017.

(Continued)

*Primary Examiner* — Igor N Borissov

(57) ABSTRACT

Infection control methods and systems associate proximity-detection devices with people in a population, such as people in a hospital. Each proximity-detection device detects proximity events with other people. The methods and systems detect proximity events and, for person-to-person pairs who were involved in such an event, records at least one risk value as a measure of risk of an infectious agent having been transferred between the pair. Upon indication of an infectious agent transfer to a member of the population, a health worker may conduct an infection control intervention on members of a subpopulation of people based on detected proximity events and risk values. The method and system may be extended to fomites. Correlations may be made over multiple infection events.

12 Claims, 8 Drawing Sheets

(56) References Cited

OTHER PUBLICATIONS

World Health Organization, "Recommendations for Investigating Contacts of Persons With Infectious Tuberculosis in Low- and Middle-Income Countries," 2012, WHO Press, World Health Organization, Geneva, Switzerland, ISBN 978 92 4 150449 2.

World Health Organization, "Implementation and management of contact tracing for Ebola virus disease," Sep. 2015, https://www.cdc.gov/vhf/ebola/pdf/contact-tracing-guidelines.pdf.

U.S. Department of Health and Human Services, Centers for Disease Control and Prevention, "Guidelines for the Investigation of Contacts of Persons with Infectious Tuberculosis," 2005, https://www.cdc.gov/mmwr/preview/mmwrhtml/rr5415a1.htm.

Olguin, D. O., Gloor, P. A., & Pentland, A. (Apr. 2009). Wearable sensors for pervasive healthcare management. In Pervasive Computing Technologies for Healthcare, 2009. PervasiveHealth 2009. 3rd International Conference on (pp. 1-4). IEEE.

Gundlapalli, A., Ma, X., Benuzilo, J., Pletey, W., Greenburt, R., Hales, J., Leecaster, M., & Samore, M. (2009). Social network analyses of patient-healthcare worker interactions: implications for disease transmission. In AMIA Annual Symposium Proceedings (vol. 2009, p. 213). American Medical Informatics Association.

Hornbeck, T., Naylor, D., Segre, A. M., Thomas, G., Heman, T., & Polgreen, P. M. (2012). Using sensor networks to study the effect of peripatetic healthcare workers on the spread of hospital-associated infections. The Journal of infectious diseases, 206(10), 1549-1557.

Lowrey-North, D. W., Hertzberg, V. S., Elon, L., Cotsonis, G., Hilton, S. A., Vaughns II, C. F., Hill, E., Shrestha, A., Alexandria, J., & Adams, N. (2013). Measuring social contacts in the emergency department. PloS one, 8(8), e70854.

Barat, A., Cattuto, C., Colizza, V., Pinton, J. F., Broeck, W. V. D., & Vespignani, A. (2008). High resolution dynamical mapping of social interactions with active RFID. arXiv preprint arXiv:0811.4170.

Barrat, A., Cattuto, C., Colizza, V., Isella, L., Rizzo, C., Tozzi, A. E., & Van Den Broeck, W. (Dec. 2010). Wearable sensor networks for measuring face-to-face contact patterns in healthcare settings. In International Conference on Electronic Healthcare (pp. 192-195). Springer, Berlin, Heidelberg.

Isella, L., Romano, M., Barrat, A., Cattuto, C., Colizza, V., Van Den Broeck, W., Pandolfini, F. G. E., Rava, L., Rizzo, C., & Tozzi, A. E. (2011). Close encounters in a pediatric ward: measuring face-to-face proximity and mixing patterns with wearable sensors. PloS one, 6(2), e17144.

Vanhems, P., Barrat, A., Cattuto, C., Pinton, J. F., Khanafer, N., Regis, C., Byeul-A, K., Comte, B., & Voirin, N. (2013). Estimating potential infection transmission routes in hospital wards using wearable proximity sensors. PloS one, 8(9), e73970.

Voirin, N., Payet, C., Barrat, A., Cattuto, C., Khanafer, N., Regis, C., Byeul-A, K., Comte, B., Casalegno, J. S., & Vanhems, P. (2015). Combining high-resolution contact data with virological data to investigate influenza transmission in a tertiary care hospital. infection control & hospital epidemiology, 36(3), 254-260.

Mastrandea, R., Soto-Aladro, A., Broqui, P., & Barrat, A. (2015). Enhancing the evaluation of pathogen transmission risk in a hospital by merging hand-hygiene compliance and contact data: a proof-of-concept study.

Lucet, J. C., Laouenan, C., Chelius, G., Veziris, N., Lepelletier, D., Friggeri, A., Abiteboul, E., Bouvet, E., Mentre, F., & Fleury, E. (2012). Electronic sensors for assessing interactions between healthcare workers and patients under airborne precautions. PloS one, 7(5), e37893.

Obadia, T., Silhol, R., Opatowski, L., Temime, L., Legrand, J., Thiebaut, A. C., Herrmann J. L., Fleury, E., Guillemot, D., Boelle, P. Y. (2015). Detailed contact data and the dissemination of *Staphylococcus aureus* in hospitals. PLoS computational biology, 11(3), e1004170.

\* cited by examiner

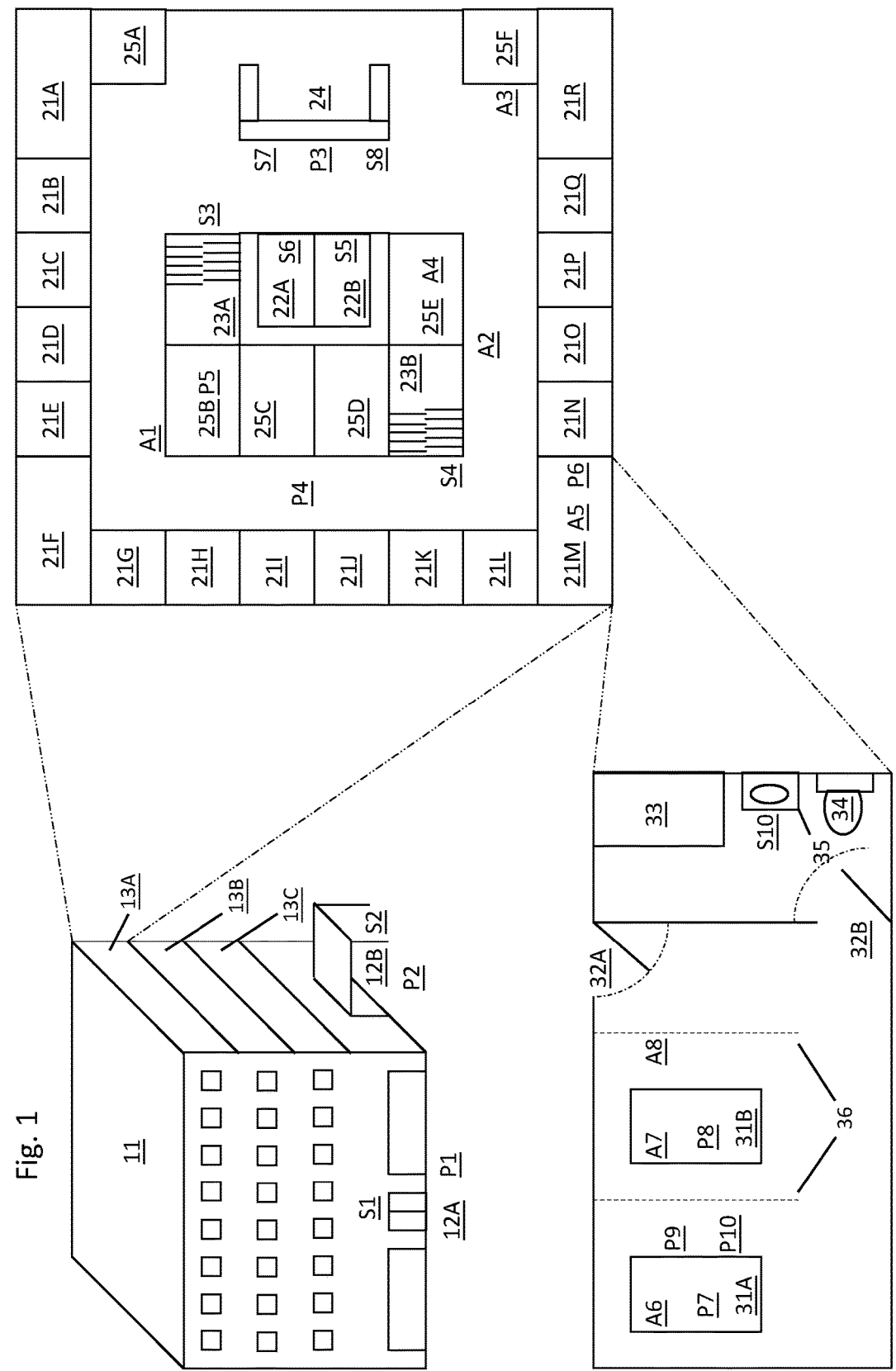

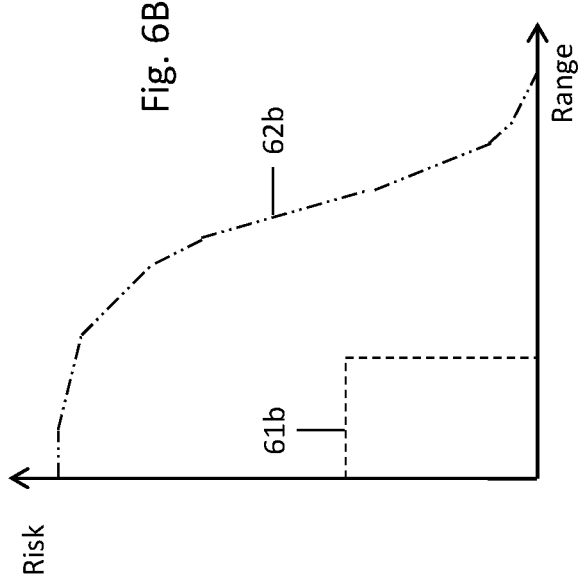
Fig. 6A
Fig. 6B
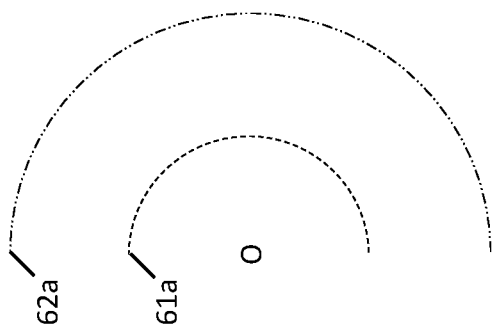
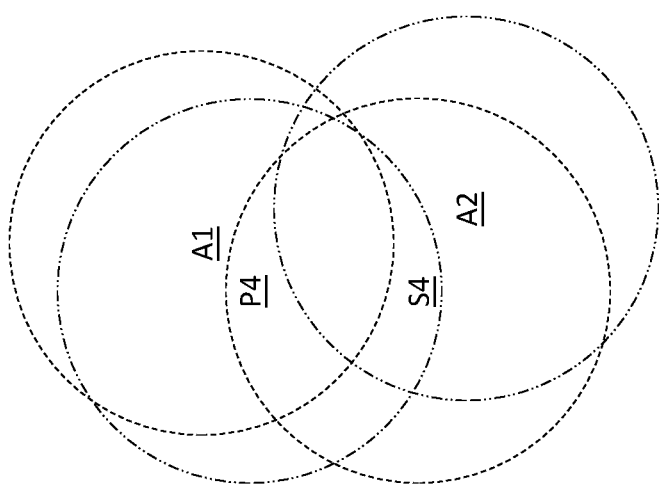
Fig. 5
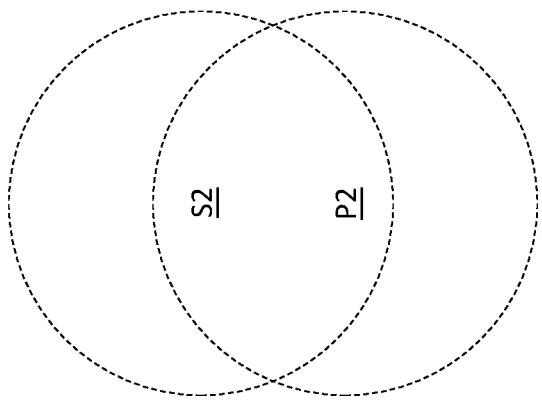
Fig. 4

90A

| 91 Event Session ID Number | |
|---|---|
| 92 Minimum Range | |
| 93A Profile Type 1 | 93B Profile Type 2 |
| 94A Profile 1 Start Time | 94B Profile 2 Start Time |
| 95A Profile 1 Duration | 95B Profile 2 Duration |
| 96A Risk Value 1 | 96B Risk Value 2 |

100A

| 101A Event ID Number |
|---|
| 102A Profile Type 1 |
| 103A Event Start Time |
| 104A Event End Time |
| 105A Minimum Range |
| 106A Risk Value 1 |

100B

| 101B EVent ID Number |
|---|
| 102B Profile Type 2 |
| 103B Event Start Time |
| 104B Event End Time |
| 105B Minimum Range |
| 106B Risk Value 2 |

PROXIMITY TRACING METHODS AND SYSTEMS

CROSS-REFERENCE TO RELATED APPLICATIONS

This application claims priority to the following U.S. provisional patent applications, each of which is incorporated herein by reference in its entirety: 62/278,983, "Contact Tracing Method and System," filed Jan. 14, 2016; and 62/364,193, "Contact Tracing Method and System," filed Jul. 19, 2016.

BACKGROUND OF THE INVENTION (1) Technical Field

This application relates to the field of infectious disease prevention and control, especially nosocomial infections in contact-intensive environments, such as health-care facilities.

(2) Background Art

In epidemiology, "contact tracing" (sometimes also called "contact investigation") traditionally has been a manual process of identifying members of a community who came into contact with an infected person for purposes of screening, diagnosis, and limiting further transmission of infectious agents. Contact tracing has sometimes been referred to as "partner notification" when used for managing sexually transmitted infections (STIs). Contact tracing has been recommended for cases of highly-infectious and dangerous diseases, such as tuberculosis, measles, smallpox and Ebola, and it reportedly has been used in the management of outbreaks of Severe Acute Respiratory Syndrome (SARS) and pertussis.

In the context of STIs, the infected person self-managed partner notification. A person who was diagnosed with an infection notified other individuals with whom the index person had sexual contact and advised them to seek testing and medical treatment if also infected.

In other contexts, a health-care worker (hereafter referred to as an "infection control official") traditionally managed the contact-trace process. When a person was diagnosed with an infection, the infection control official asked the person (hereafter referred to as an "index case") about other people with whom the index case came into contact. Those individuals (hereafter referred to as "first-tier contactees") could be treated prophylactically and/or observed for symptoms of sickness for a period of time, which usually would be the incubation period for the infection. If a first-tier contactee showed no symptoms of infection during the incubation period, that person was not at risk of developing the illness from contact with the index case and no longer needed to be monitored. If a first-tier contactee did show symptoms, that first-tier contactee would be treated medically for the illness, and the infection control official would repeat the contact-trace process using the then-symptomatic, first-tier contactee as an index case. That is, the infection control official would ask the first-tier contactee about other people with whom the first-tier contactee came into contact. All those people then could be treated prophylactically and/or monitored for symptoms of sickness. The process would repeat recursively through additional tiers of contactees until all contactees at all tiers were either treated or passed the monitoring period without developing symptoms of illness.

BRIEF DESCRIPTION OF THE DRAWINGS

Reference will be made to the following drawings, which illustrate preferred embodiments of proximity tracing methods and systems as contemplated by the inventor.

FIG. 1 illustrates a facility for deployment of the disclosed proximity-tracing methods and systems.

FIG. 2 illustrates further detail of a floor plan of the facility of FIG. 1.

FIG. 3 illustrates further detail of a room of the floor plan of FIG. 2.

FIG. 4 illustrates proximity zones of a person and a site illustrated in FIG. 1.

FIG. 5 illustrates proximity zones of a person, a site, and apparatus illustrated in FIG. 2.

FIGS. 6A and 6B illustrate risk functions for two transmission modes.

Figure 7:
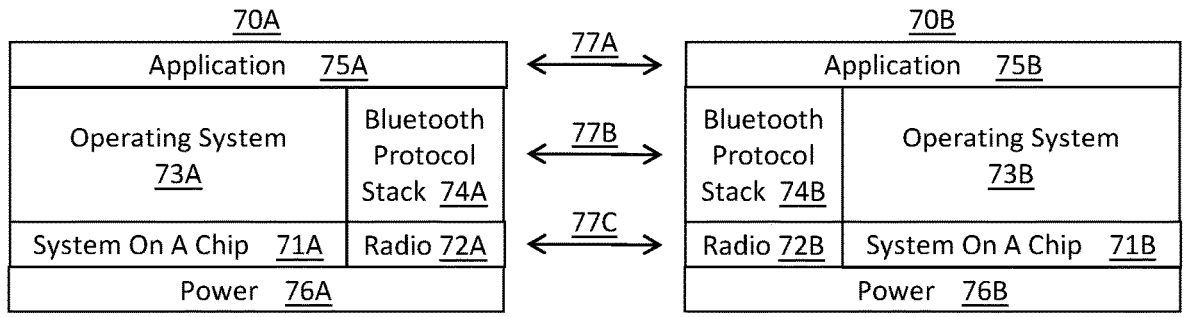
FIG. 7 illustrates an architecture for electronic tags.

The drawings and these descriptions thereof are simplified for convenience of explanation, and inclusion or exclusion of specific details or features is not intended to limit the scope of proximity-tracing methods and systems.

DETAILED DESCRIPTION OF THE INVENTION

The methods and systems described below have particular utility for reducing rates of transfer of infectious agents in environments that are either favorable for transmission of infectious agents or where impacts of such transmission are severe in terms of financial cost or human suffering. Such environments include contact-intensive environments where people live or work in close proximity, where drug resistant pathogens can be problematic, or where enhanced precautions are desirable to reduce infection transmission. Examples of such environments include health-care facilities (including hospitals, clinics, rehabilitation centers, assisted living facilities, nursing homes, etc.), confined institutions (including prisons, schools and military environments), cruise ships, food-processing centers, infectious disease research laboratories, etc.

FIG. 1 illustrates a generic facility 11 suitable for deployment of proximity-trace methods and systems. FIG. 1 illustrates an exemplary building 11 with multiple entrances 12A, 12B and multiple floors 13A-13D. The character "P" followed by a numeral distinguishes different people, e.g., "P1", "P2", etc. The character "S" followed by a numeral distinguishes sites of interest, e.g., "S1", "S2", etc. For example, FIG. 1 depicts a side door labeled "S1" and a front entrance (with awning) labeled "S2". "P1" depicts a first person near the side entrance "S1," while "P2" depicts a second person near a front entrance "S2."

FIG. 2 illustrates further detail of an exemplary floor plan of the facility of FIG. 1. FIG. 2 illustrates a simplified hospital ward with patient rooms 21A-21R along perimeter walls. Elevators 22A, 22B and stairways 23A, 23B provide access to the ward. A nursing station 24 may provide a base of operations for nurses and other hospital staff. Other supporting rooms 25A-25F may serve other functions, such as storage, staff break room, meeting room, etc. The character "A" followed by a numeral depicts mobile inanimate objects, hereafter referred to generically as "apparatus," e.g., "A1", "A2", etc. Such apparatus may include movable beds and gurneys, wheelchairs, IT computers on rolling stands, medical diagnostic and treatment equipment (e.g., crash carts, ventilators, oxygen tanks, etc.), food delivery carts, repositionable hand sanitizer stations, etc. Hereafter, people, sites, and apparatus will be referred to by their alphanumeric designations without quotations. FIG. 2 illustrates a number of distinct points of interest: stairway doorways "S3," "S4," elevators "S5," "S6," and opposite corners "S7," "S8" of nursing station 24. FIG. 2 additionally illustrates several people: "P3" at the nursing station 24; "P4" in a hallway; "P5" in a supporting room 25B; and "P6" in a patient room 21M. FIG. 2 further illustrates several pieces of apparatus: "A1," "A2" and "A3" in hallways; "A4" in an auxiliary room 25E; and "A5" in patient room 21M.

FIG. 3 illustrates further detail of a patient room 21M of the floor plan of FIG. 2. FIG. 3 illustrates an exemplary, double room with hallway door 32A, washroom door 32B, two patient beds 31A, 31B, wash tub 33, commode 34, and sink 35. The beds 31A, 31B additionally are labeled as apparatus "A6," "A7," and the sink 35 is labeled additionally as a site "S10." Patients "P7," "P8" are shown in beds "A6," "A7" respectively. Additional people "P9," "P10" are next to bed 31A as, for example, a nurse and doctor consulting with patient "P7." An additional piece of apparatus "A8" is adjacent bed 31B as, for example, a supplemental oxygen tank for a patient. Beds may be screened by curtains 36.

These people, sites, and apparatus illustrated in FIGS. 1-3 are merely examples for illustration purposes, and substantially higher numbers and densities should be expected. It should be understood that people and apparatus may move about the facility over time, and sites of interest may be added or deleted over time. FIGS. 1-3 exemplify a single moment in time for illustration purposes only. A wide variety of people, apparatus, and sites may be present.

Each person, apparatus, and site of interest will bear an electronic tag as described further below. The term "tag" here means an electronic device used for detecting proximity. A tag may be wearable by people, mobile for movable apparatus, or fixed for sites and stationary apparatus. Tags may be affixed permanently, such as by physical attachment to sites and apparatus, or they may be attached temporarily, such as by lanyard or identification badge to a person.

Tags are used to detect "proximity," which here means a one-dimensional range or surrogate measure of range, including touch contact. Proximity will be detected as people and apparatus approach one another and fixed sites. Proximity detection will be lost as people and apparatus move away from one another and fixed sites. The term, "session," will be used here to mean a contiguous period of time during which proximity is detected. The beginning and ending of sessions may vary from tag to tag, location to location, and time to time. Sessions will preferably, but not necessarily be pairwise in that, if a first tag detects proximity to a second tag, the second tag will also detect proximity to the first tag. However methods and systems may capture only a single data set for a session.

The discussion below sometimes will refer to behavior of tags, as distinct from behaviors of people, sites, and apparatus. For convenience of reference, tags will be identified by their associated person, site or apparatus. For example, "tag P1" (as distinct from "person P1") will hereafter be used to refer to a tag associated with person P1, "tag S1" will refer to a tag associated with site S1, "tag A1" will refer to a tag associated with apparatus A1, and so on.

FIG. 4 conceptually illustrates proximity zones of tags affixed to a person P2 and a site S2 as illustrated in FIG. 1. "Proximity zone" here means a region in which proximity is detected. FIG. 4 illustrates a first proximity zone 41 as bounded by a dashed line centered on person P2, and a second proximity zone 42 as bounded by a second dashed line centered on site S2. This could exemplify a person P2 at an entrance S2 to a hospital as illustrated in FIG. 1. In FIG. 4, person P2 is within the proximity zone of site S2, and vice versa. A proximity zone need not be circular or even fixed in dimension, either from tag to tag, place to place, or time to time, because factors other than distance affect ranges at which proximity may be detected. In a hallway, for example, a proximity zone may extend a relatively long distance along the length of a hallway but only a short distance laterally to hallway walls. FIGS. 4-6 illustrate proximity zones as circles for easy of illustration only.

FIG. 5 illustrates proximity zones of tags A1, P4, S4, and A2 corresponding to entities illustrated in FIG. 2. This could exemplify a person P4 in a hallway between a stairway entrance S4 and a hand-sanitizing station A1. Apparatus A2 may be a computer work station on rolling stand. Tag A1 and tag S4 are within the proximity zone of tag P4, but tag A2 is sufficiently far away and around a corner from tag P4 that it is outside the proximity zone of tag P4. Analogously, tag A1 is outside the proximity zone of tag A2, and tag A2 is outside the proximity zone of tag A1, but tag S4 is within the proximity zone of tag A2. Presence or absence of tags within proximity zones may change moment-by-moment as people and apparatus move about the ward and as tags are added or removed from sites. Again, proximity zones are shown as equal in diameter, but these diameters are for illustration purposes only and should not be interpreted as signifying that all proximity zones are, or must be, equal in physical dimension. To the contrary, proximity zones are likely to vary from tag to tag, from time to time, and from location to location.

As mentioned above, a "session" between one tag and another means a contiguous period of time during which proximity is detected. A session may be considered a time period during which one tag is within a proximity zone of another tag, such as illustrated in FIGS. 4-5. For a tag that senses proximity using a frequency hopping radio signal, a session may be a time period during which tags maintain synchronization.

A feature of the disclosed methods and systems is a capability to characterize proximity sessions in more useful ways than binary presence and absence. Not all sessions are equally probable for transmitting an infectious agent, nor are two otherwise-identical sessions (in terms of time and range) equally probable for transmitting all types of infectious agents. Multiple factors can affect probability of transmission including, without limitation, duration of a session, ranges achieved during a session, activity of the tag bearer, and the nature of the infectious agent itself. For example, a first session might last only ten seconds and have a point of closest approach of several meters. This might occur when a first health-care worker sits at a nursing station and another worker passes by without stopping. In contrast, a second session might last fifteen minutes during which separation distance closes to less than one meter multiple times. This might occur when a nursing aid assists a patient with bathing and other daily-living activities. The second session has a higher risk of transferring an infectious agent than the first. By way of further example, infectious agents have different modes of transfer. Some require touch contact to transfer. Others are carried by relatively large moisture droplets, such as by a cough, and can carry for distances of several meters. Still others are airborne and can be transferred across longer distances. The first session discussed above has a higher risk of transmitting an airborne virus than a bacteria that can only be transferred by touch contact.

FIG. 6A illustrates two generic zones for understanding relationships between range and risk for transfer of infectious agents. An inner zone 61a centered on point "o" represents a person's reach radius. An outer zone 62a represents an imaginary range for transferring agents by suspended air droplets, like coughing. The range at which a touch contact agent can be transferred is sharply delineated, because a person's reach radius is relatively fixed. However, the range at which expelled cough droplets could carry agents is not fixed. The transfer range for droplets is more like a probability function that diminishes with distance. FIG. 6B illustrates potential risk functions for touch- and droplet-transfer modes. Line 61b illustrates a touch-transfer risk function. The probability of a transfer is relatively constant within the reach radius, but drops to zero outside the reach radius. Line 62b illustrates a droplet-transfer probability function. The probability of a transfer is higher at closer ranges and lower at farther ranges, because concentrations of droplets fall at farther ranges, but vary continuously without a sharp cutoff.

Preferred tags are adapted to measure ordinal parameters correlated with probabilities of transferring infectious agents. "Ordinal" parameters have ordered values, like range and time. (In contrast, "nominal" parameters have values which are not ordered, such as hair color.) For each session between each pair of tags, the disclosed methods and systems measure and record one or more ordinal values, hereafter called "Profile Risk Values," which vary according to probabilities that an infectious agent was transferred during the session. Ordinal values may be continuous or vary discretely over a number of quantized intervals. Each Profile Risk Value corresponds to a different infectious agent, class of agent, or mode of transmission. In a simple form, the methods and systems may record a first Profile Risk Value for infectious agents with a transfer mode of physical touch, and a second Profile Risk Value for infectious agents carried through the air. Infectious agents carried through the air may be further divided into separate profiles for (i) those that transfer through large droplets and (ii) airborne ones that can carry for longer distances. Other profiles may be used. Preferred Profile Risk Values take into account multiple ordinal parameters correlated with risk, though they may also include components derived from nominal parameters.

By way of a first example, a generic profile may be an integral (or summation over discrete time intervals) of range, e.g.: $PV1 \sim \Sigma (\Delta t/r)$, where "PV1" is a first Profile Risk Value, "r" is the range between tags, and $\Delta t$ is the duration of a discrete time interval over which the range was measured or between measurements. The symbol "~" means proportional, which permits additional factors. In general, the closer the range, and the more time spent at a closer range, the greater the likelihood of transfer of an infectious agent. Values of range ("r") may be limited to some non-zero minimum to avoid errors from dividing by zero.

By way of a second example, a second profile may use a weighted integral (or weighted sum over discrete time intervals) of range, e.g.: $PV2 \sim \Sigma (\Delta t/f_1(r))$, where $f_1(r)$ is function giving different weights to different ranges. For a profile directed to a touch-contact infectious agent such as Ebola, $f_1(r)$ may have a value of infinity (or simply not be counted) for ranges greater than about two (2) meters and a value of range (r) for ranges less than about two (2) meters.

By way of a third example, the weighting function may be more smooth but give ever increasing weight to closer proximity, such as by a square law, e.g.: $PV3 \sim \Sigma (\Delta t/r^2)$. Other profiles may use different parameters and different weighting functions as appropriate for different infectious agents and circumstances, such as weighting functions derived from risk functions shown in FIG. 6B.

FIG. 7 illustrates an architecture for two exemplary tags 70A, 70B for use in proximity-tracing methods and systems. Each such tag includes a programmable computing machine 71A, 71B, such as a so-called "system on a chip" or "compute module" having one or more programmable computer processing cores, memory, and associated circuitry. Each tag includes one or more sensors, which in this case is illustrated as radios 72A, 72B. Received radio signal strength has advantages as a measure of range, though other sensors may be used, such as ultrasonic transmitters/receivers, infrared transmitters/receivers, radar (including Doppler radar), or other sensors not listed or yet envisioned. Relative range between two tags also may be determined indirectly. For example, a first device may be used to detect proximity or position relative to a reference location, a second device may be used to detect proximity or position relative to the same or a different reference location (whose position is known relative to the first reference location), and range between mobile devices may be determined by triangulation or other calculation based on the two devices' measurements relative to intermediate reference locations(s). Proximity or position may be determined in two- or three-dimensional frames of reference, by Cartesian or other coordinate systems (e.g., range and bearing), or by other measurements.

Proximity-tracing methods and systems preferably use received radio signal strength values, or estimated signal loss, as a surrogate measure of range. Signal strength may be, but need not be, converted to range using signal propagation or loss models. Transmission power may be fixed for all tags, or a transmitting tag may vary its transmission power and communicate its power value to a receiving tag so that the receiving tag may compute a difference between transmitted and received power.

A preferred radio channel access scheme for range measurement is a frequency-hopping technique in which each radio 72A, 72B rapidly changes its transmission frequency among multiple channels. Each pair of such tags will negotiate a unique sequence of hops at the beginning of their session and synchronize their transmissions. When a tag has multiple neighbor tags in its proximity zone, the tag may make individual ranging measurements with each neighbor tag by negotiating distinct hopping sequences with each neighbor tag. For example, tag 70A may synchronize with tag 70B using a first hopping sequence, and each tag 70A, 70B would measure received signal strength over one or more of those frequency-hopping cycles. Tag 70A may then synchronize with another tag (not show) using a different hopping sequence. Clashes (i.e., simultaneous transmissions by different tags at the same frequency) may cause erroneous signal measurements. However, such clashes will likely be only for a duration of one or a small number of hops. The error will appear as noise in the measurement and treated accordingly. By measuring received signal strength of frequency-hopping transmissions, multiple tag pairs may concurrently make range measurements. From signal strength and an internal clock for measuring time intervals between measurements, such tags may produce one or more non-binary, ordinal Profile Risk Values. Parameter measurements and Profile Risk Values may be discretely varying, such as produced by analog-to-digital converters that make quantized measurement of signal strength, and by digital computers performing digital computations on those quantized measurements. Time measurements also may be quantized into sampling intervals, and such intervals may be fixed or variable.

Benefits of a frequency hopping method can be appreciated from a situation illustrated in FIG. 3. There, tags A6, P7, A7, P8 and A8 all are within proximity zones of one another. Tag A6 may measure signal strength with tag P7 on a first hoping pattern, and tag A7 may simultaneously measure signal strength with tag P8 on a different hopping pattern. Tag A6 may then sequentially synchronize with A7, then P8, then A8, etc., while other tags sequentially make measurements for all permutations of tag pairs.

Other frequency utilization schemes may be used. For example, tags may time-share a limited number of channels, such as three so-called advertising channels as defined by the Bluetooth Low Energy frequency allocation scheme. Alternately, tags may make initial discovery of other tags by advertising on one or more of a limited number of channels (e.g., Bluetooth Low Energy advertising channels), and the switch to pair-wise ranging using other channels (e.g., Bluetooth Low Energy data channels.)

An exemplary tag may be made by adapting general-purpose products intended for communications, such as using the Bluetooth communication standard as maintained by the Bluetooth Special Interest Group. Although Bluetooth was developed for communicating data rather than characterizing risk of disease transfer, the Bluetooth standard specifies protocols for frequency hopping radios and controllers which are produced in relatively high volume at relatively low cost. Some products can be obtained with integrated operating systems 73A, 73B and Bluetooth Protocol Stack 74A, 74B, which provides software control over the radios 72A, 72B, among other functions. The Bluetooth specification includes a multilayer communication protocol. A lower layer specifies a physical connection 77C between devices, including frequency hopping and synchronization. An intermediate layer 77B provides for one or more data transport protocols. An additional layer 77A may be added between applications 75A, 75B, for example to communicate transmit power. Such products may be adapted to the proximity-tracing methods and systems disclosed herein by way of application programs 75A, 75B exercising control of the radios 72A, 72B through a Bluetooth Protocol Stack application program interface (API). An exemplary starting product would be an INTEL™, EDISON™ brand compute module with integrated Linux operating system and BlueZ Bluetooth protocol stack. Applications 75A, 75B may be written in the "C" programming language or a "C" derivative, such as C++, to provide novel functionality described here for proximity tracing. Alternately, tags may be made from other general purpose products (present or future), other programming languages, or by way of custom circuitry. Compute modules can be packaged to receive power 76A, 76B from fixed or mobile sources, including batteries.

Figure 8:
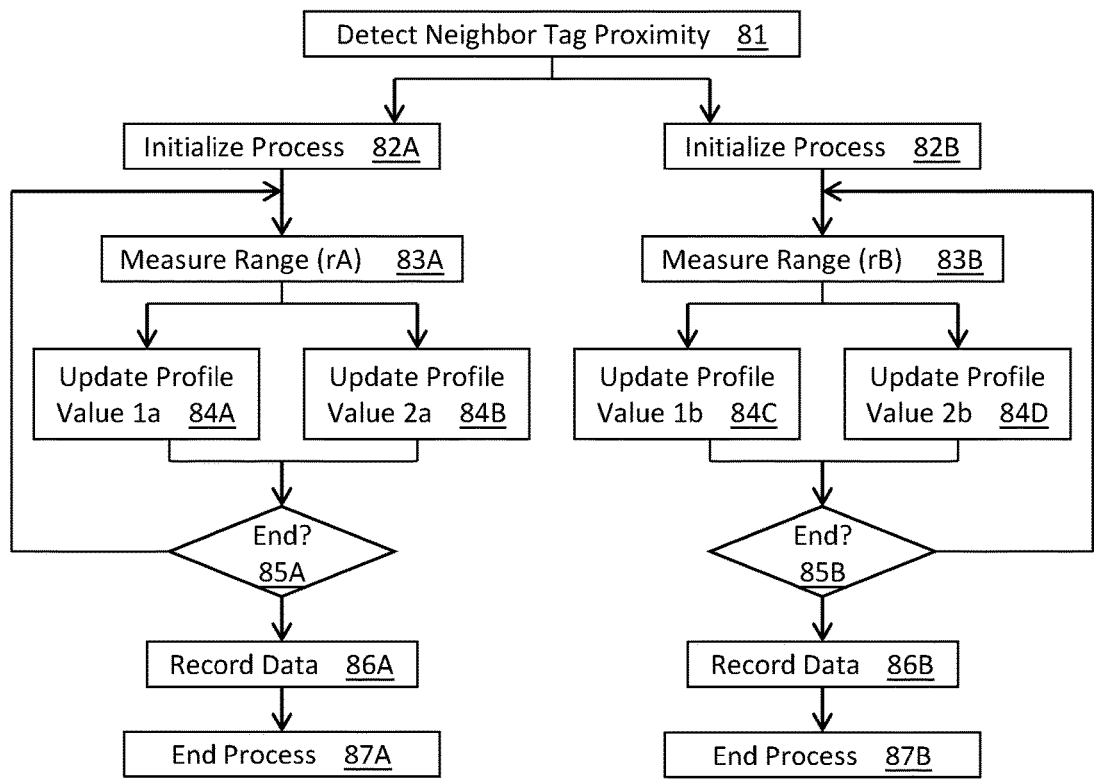
FIG. 8 illustrates a method performed by tags for updating Profile Risk Values.

FIG. 8 illustrates an application-layer method for measuring proximity parameters and generating Profile Risk Values. In a preferred method, each tag performs the illustrated method. The tag performing the method will be referred to as the "host" tag, while other tags in the host tag's proximity zone will be referred to as "neighbor" tags. In a proximity detection step 81, a host tag detects the presence of one or more neighbor tags, such as by using a Bluetooth inquiry or scanning process as defined in the Bluetooth standard. Detection could demark the beginning of a session. The host tag initiates a distinct process 82A, 82B for each neighbor tag detected. While FIG. 8 illustrates two processes, the number of processes may vary over time as neighbor tags appear and disappear from the host tag's proximity detection zone. In a frequency hopping system as discussed above, the host tag may synchronize with a first neighbor tag in a first process and measure signal strength as a measure of range over one or more hopping cycles 83A. The host tag then updates Profile Risk Values 84A, 84B using a first measured range value rA. The host tag then can synchronize with a second neighbor tag in a second process and measure signal strength 83B over one or more hopping cycles which follow a different hopping pattern from the first. The host tag then updates Profile Risk Values 84C, 84D using a second measured range value rB. The host tag continues to update Profile Risk Values throughout each proximity session. When the host tag no longer detects a previously-detected neighbor tag, the host tag makes a decision 85A, 85B to end the update process for that tag. The host then records the Profile Risk Value(s) 86A, 86B and ends the process 87A, 87B. The host tag also may transmit session data to a database as discussed further below. Multiple update processes may begin and end separately as neighbor tags enter and leave a host tag's proximity zone. Measurement of proximity parameters with all neighbors may be coordinated in a single process.

While FIG. 8 illustrates two Profile Risk Values, a host tag may update additional Profile Risk Values using different risk functions. Furthermore, a host tag may engage in multiple sessions with the same neighbor at different times as those tags move into and out of the host tag's proximity zone.

Figures 9, 10, 11:
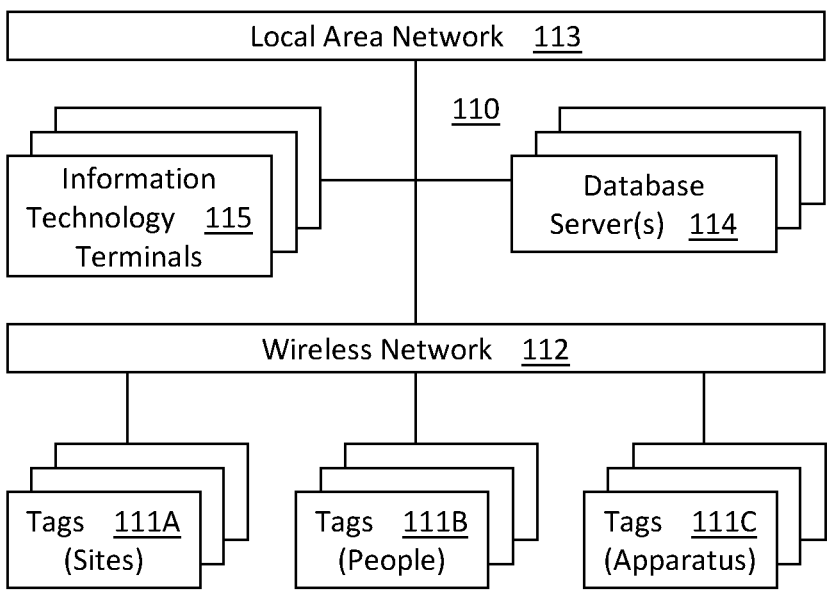
FIG. 9 illustrates data fields for proximity events, including two Profile Risk Values.
FIG. 10 illustrates alternate data fields for proximity events, including two Profile Risk Values.
FIG. 11 illustrates a system for storing and retrieving proximity information.

FIG. 9 illustrates an exemplary data record 90A for recording risk Profile Risk Values from a session. Each session receives a unique session identification number 91 which may be derived from unique identification numbers of tags involved in the session and the date of the session, including time of day when the session starts. Each session preferably (but not necessarily) includes a minimum range measurement 92 detected during the session. For each Profile Risk Value, the session record includes a profile type 93A, 93B, a start time 94A, 94B, a duration 95A, 95B, and a Profile Risk Values 96A, 96B. FIG. 9 illustrates two Profile Risk Values, but additional Profile Risk Values may be included. Profile Risk Values may be derived over different time periods within a single session. For example, if a nurse moves into proximity with a patient but does not immediately close to within touch contact range, the Profile Risk Value for an airborne infectious agent may increase over the entire period of the session, while a Profile Risk Value for a touch-contact agent may increase only over the period when the nurse was within touch range.

FIG. 10 illustrates alternate data records for Profile Risk Values. The format of FIG. 10 generates separate records 100A, 100B for each Profile Risk Value of each session.

Each record 100A, 100B includes a unique event identification number 101A, 101B, an identification of the profile type 102A, 102B, a start time when the profile criteria were satisfied 103A, 103B (if not part of the identification number 101A, 101B), an end time when the profile conditions were no longer satisfied 104A, 104B, a minimum range measurement 105A, 105B, and a Profile Risk Value 106A, 106B. FIG. 9 illustrates two Profile Risk Values, but additional Profile Risk Values may be included. Other record formats and content may be used besides those of FIGS. 9 and 10.

FIG. 11 illustrates an exemplary system 110 for storing and retrieving proximity event information. Multiple tags for sites 111A, people 111B and apparatus 111C connect to a wireless network 112 using a standard communication protocol, such as WiFi or Bluetooth. The wireless network in turn may connect with a local area network 113 and/or other network systems which may be local to, or remote from, the wireless network 112. One or more database servers 114 also connect to the network, directly or indirectly, preferably by wired interface though a wireless interface is not prohibited. Information terminals 115 may be used to access the database for administrative purposes and to identify tags (and hence their associated people, apparatus, and sites) for infection control intervention.

Figure 12:
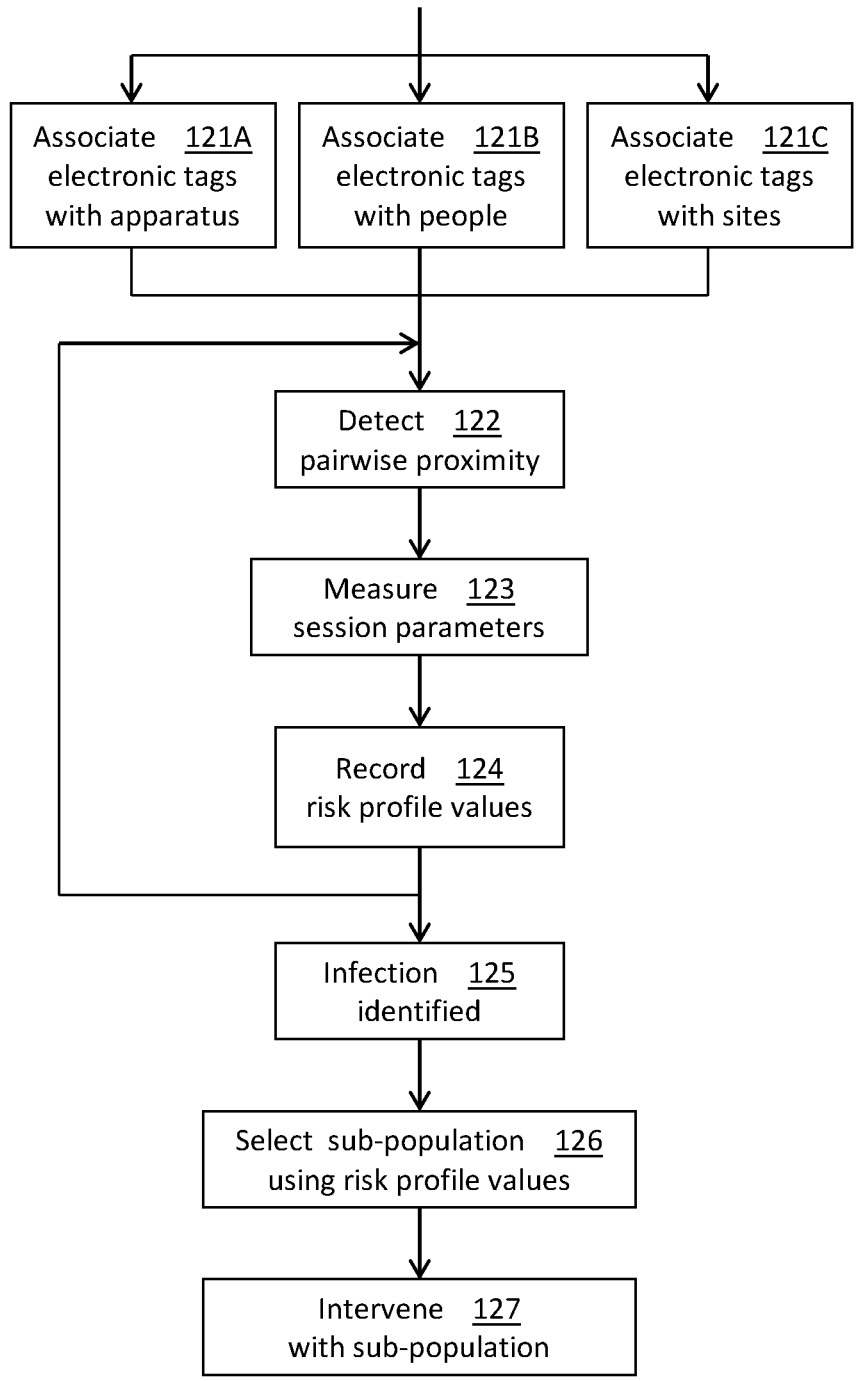
FIG. 12 illustrates steps in a proximity-tracing intervention.

FIG. 12 illustrates steps in an exemplary intervention method. The method begins with steps of associating tags with apparatus 121A, people 121B, and sites 121C as discussed above. In real time, tags are used to detect proximity in pairs of host and neighbor tags 122. For each session, each host tag measures session parameters 123, such as signal strength and time intervals. When a host tag no longer detects a neighbor tag, the host tag records Profile Risk Values 124. The recording step 124 may include recording within memory of the tag and/or recording in a database remote from the tag.

It is expected that the steps above will repeat to provide real-time and ongoing detection of neighbors and recording of session data for all tags in the system over extended periods of time (on the order of weeks, months or more). At some time after initiation of the method, a person, apparatus, or site (referred to here as an "index entity") may be recognized as being infected or carrying an infectious agent 125. An infection control official may then query the database to identify the tag associated with the index entity. The infection control official may then further query the database to identify other entities that came into proximity with the index entity in a relevant way for intervention. People, sites, and apparatus associated with those tags then form one or more sub-populations (out of sets of all people, sites and apparatus) as candidates for intervention 126. The infection control official may then intervene 127 with the subpopulation(s). The specific intervention protocol will depend on the infectious agent involved. If vaccines are available for the infectious agent, intervention may involve vaccinating members of a human sub-population. If vaccines are not available, members of the human sub-population may be monitored and/or isolated. Apparatus and sites may be disinfected using disinfectants appropriate to the infectious agent.

By way of specific example, solely for simplified illustration purposes, a hospital as illustrated in FIGS. 1-3 may use the disclosed methods and systems by providing tags to all hospital staff, patients, and visitors. The hospital may also affix tags to mobile equipment that could come into proximity with those people, and sites where infectious agents might be likely to form reservoirs. Tags may monitor for two generic profiles of infectious agents: airborne and touch-contact agents. The airborne profile may use a Profile Risk Value that is proportional to the discrete sum of time interval divided by range over an entire session. The touch-contact profile may use a Profile Risk Value that is proportional to the discrete sum of time interval divided by range while range is less than about 2 meters. Over time, the system will record proximity event information for all tags for the two profiles in a database.

At some later point in time after system initiation, a patient (e.g., P7, FIG. 3) may be diagnosed with MRSA, which is managed as a touch-contact infectious agent. This patient will be referred to here as the "index patient." Upon diagnosis, an infection control official would initiate medical treatment and enhanced infection control protocols for the index patient, such as isolating that patient from the general population and requiring all care givers to wear caps, gowns, and gloves while in the isolation area.

During the time before the index patient was diagnosed, the index patient might have shed MRSA to other people, sites, and apparatus with which the index patient came into touch contact. Those people, sites and apparatus may in turn further transmit MRSA as they touch, or are touched by, others. Such transfers will be referred to as "secondary transmissions." In order to limit and neutralize these secondary transmission, at the time of diagnosis of the index patient, an infection control official would query the database for proximity events with the index patient meeting the touch-contact profile criteria since the time the index patient was admitted. For the example of patient P7, first-tier touch contact events may have been recorded for the patient's bed A6, a nurse P9, and a doctor P10, and sink S10 if tagged. The database query might also show a touch-contact event with apparatus A3 (FIG. 2), which might have been a wheelchair used temporarily to transport patient A6 but which was not in the room 21M at the time of diagnosis. Nurse P9 may have had dozens of touch-contact events with cumulative times of hours, while doctor P10 might have only a few touch-contact events with cumulative times of tens of minutes. The infection control official may require disinfection of the nurse P9, the doctor P10, all apparatus that was in the room A3, A6, A7, A8, and terminal cleaning of the room 21M.

The infection control official also could query the database for second-tier contacts, e.g., other contactees with nurse P9, doctor P10, or apparatus A3, which may have left the room 21M and transported MRSA bacteria elsewhere in the ward. Such searches might reveal a large number of other patients with whom, or with which, the nurse P9, doctor P10, and apparatus A3 had touch-contacts. The infection control official might not have resources to disinfect all contactees and rooms of contactees where secondary transmissions might have occurred. In fact, not all contact events necessarily transmitted MRSA, and an overly-extensive intervention might waste limited resources. The infection control official might choose to test the ten, highest-risk contactees (people or fomites) for MRSA. If any of them is found to bear MRSA bacteria, the infection control official may repeat the intervention protocol using the newly-discovered, infected entities as index entities.

Proximity tracing is a tool which may be used in different ways according to the nature of the infectious agent and other factors. For many diseases, the relevant time period may be the disease incubation period, though for others it may be different, such as the entire time the patient was in the facility. The intervention protocol may vary according to risk level of each contactee as evidenced by recorded Risk Profile Values. High-risk contactees may be isolated and/or disinfected, while lower-risk contactees might be selected for a lower level of response, such as wearing protective clothing (mask, gown, glove) until tested. "Contactees" here includes entities with which the patient had recorded proximity events and may include people and fomites.

Use of risk profiles is especially beneficial in dynamic environments where the number of proximity events during a relevant time period might otherwise be overwhelming relative to infection-control resources. An infection control official can manage limited resources by ranking the sub-population(s) by Profile Risk Value. This has two immediate benefits. First, it provides general management information about the nature and extent of potential secondary transmissions. If numerous, high-risk events appear in a query, an infection control official may choose to notify management and seek additional resources. Second, it lets the infection control official prioritize those members of the sub-population(s) which are most likely to be sources of secondary transmissions.

Figure 13:
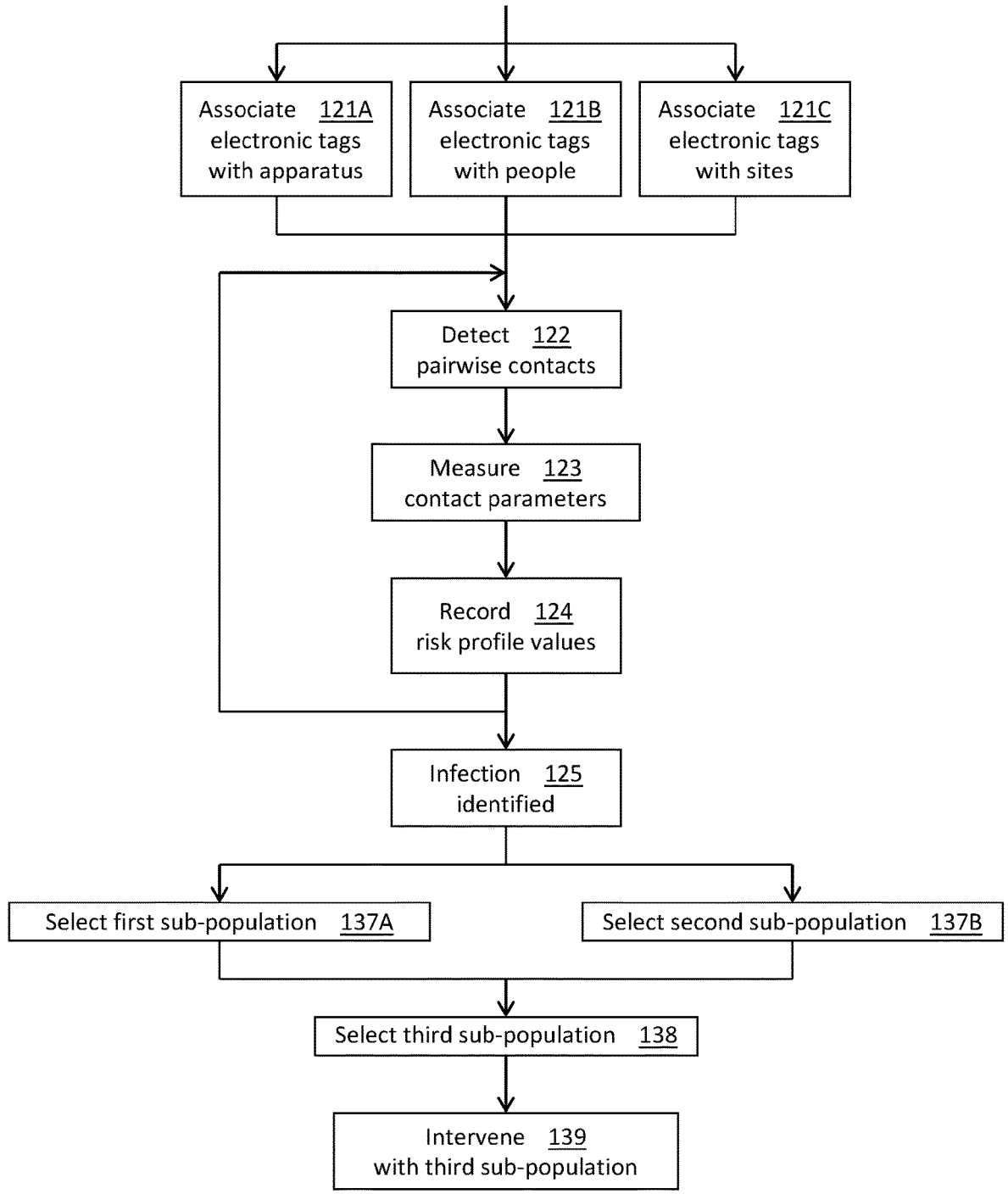
FIG. 13 illustrates steps in a correlative proximity-tracing intervention.

FIG. 13 illustrates steps in a correlative proximity-tracing intervention method. The methods described above in connection with FIG. 12 are useful for responding to a specific infection case, however, proximity-tracing methods and systems can also assist in identifying recurrent sources of infectious agents within a population. Recurrent sources may include sites within a facility which are not effectively disinfected by routine cleaning, and workers who recurrently carry infectious agents into the facility from the community or otherwise cause infections.

The method of FIG. 13 begins similarly to the method of FIG. 12 up to the point of infection identification 125. FIG. 13 uses identical reference numerals for common preliminary steps 121A, 121B, 121C, 122, 123, 124, 125. Upon identification of an infectious agent transfer to a first index entity 125 (person or fomite), an infection control official queries the database to identify a first subpopulation of relevant contactees 137A. The infection control official also conducts queries into one or more potentially-related, past cases of infection to obtain a second sub-population 137B of contactees from a different period of time. Past cases may be of the same or different index entities or be related by type. For example, if a hospital unit detects a central line associated blood stream infection ("CLABSI"), the infection control official may search prior CLABSI infections or prior infections attributed to the same infectious agent, whether CLABSI or otherwise. If a common source was causally related to both infections, that common source would be expected to appear in both the first and second sub-populations. The infection control officer might select a third sub-population 138 made up of contactees (persons and/or fomites) present in both the first and second sub-populations and intervene with those common contactees. For example, if a particular site recurrently appears in multiple queries for multiple MRSA infections over time, the infection control officer might test that site and/or increase the disinfection frequency for that site. Alternately, if a particular person recurrently appears in multiple queries for a particular agent, the infection control officer may choose to initiate periodic screening or other surveillance of that person, provide additional training, or other intervention action.

Figure 14:
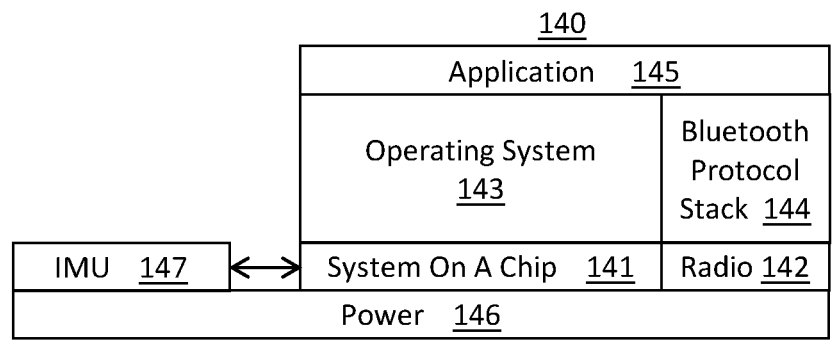
FIG. 14 illustrates an alternative architecture for electronic tags.

FIG. 14 illustrates an alternative architecture for an electronic tag 140 for use in the disclosed proximity-tracing methods and systems. Similar to tags illustrated in FIG. 7, a tag as in FIG. 14 includes a programmable computing machine 141, such as a so-called "system on a chip" or compute module having one or more programmable computer processing cores, memory, and associated circuitry. Each such tag may include one or more sensors, one of which is illustrated as radio 142. Tags preferable include an operating system 143 and Bluetooth Protocol Stack 144 which provides software control over the radio 142, among other functions. General purpose products, such as an INTEL™, Curie™ brand system-on-a-chip may be adapted to the proximity-tracing methods and systems disclosed herein by way of application program 145 exercising control of the radios 142. An application 145 may be written in the "C" programming language or a "C" derivative, such as C++, to provide novel functionality described here for proximity tracing. The Curie™ brand chip includes an integrated, 3-axis accelerometer which may be used as a motion sensor. Other motion sensors may be used, such as one or more inertial measurement units (IMUs) 147, which may measure specific force and/or angular rates. External sensors may be integrated into a single package sharing power 146, or they may be packaged separately with their own power and communication link. External IMUs may be Micro-Electro-Mechanical Systems (MEMS). Tags also may be augmented with position sensors that determine position relative to an external frame of reference.

Figure 15:
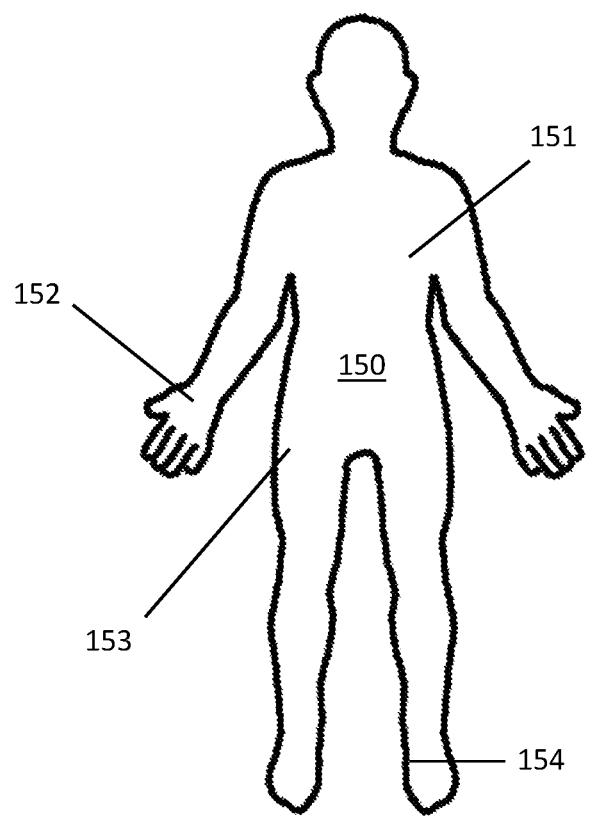
FIG. 15 illustrates potential tag placement on a human body.

FIG. 15 illustrates potential sensor placements on a human body 150. Exemplary placements may include sites where a motion sensor predominantly detects center-of-mass motion, such as on a chest 151 or hip 153. Alternate sensor placements may include sites where a motion sensor more strongly detects motion of an extremity, such as on a wrist 152 or ankle 154. Such extremity placements may be used to more easily characterize non-translational activities, such as getting in and out of bed, hand-washing, etc. Multiple sensors may be used, such as on a torso and wrist. Where one sensor is integrated into a tag and other sensors communicate their respective readings to the tag, the tag may combine readings to make a single risk value for each Risk Profile. Where each sensor is integrated into a different tag, tags may establish a communication link, with one tag acting as a master and combining readings to report a single value for each Risk Profile.

Tags may be identical for all entities in a system, or they could be adapted for specific uses. Wearable tags may be carried on people by lanyard, integrated into identification badges, or worn in other ways. They may use relatively low power mobile electronics with replaceable or rechargeable batteries. Other types of devices could be adapted for use as tags, such as cellular phones and personal digital assistants, using programmed applications (commonly called "Apps").

Tags can improve operations using acceleration or other motion sensors relative to tags without. For example, tags which remain motionless for long periods of time may self-identify as attached to fixed sites or static apparatus rather than as attached to moving people or mobile apparatus. Such tags may alter their sensor and other activity accordingly, such as by making sensor measurements less frequently to preserve power and reduce interference.

Tags also can improve risk assessment with motion sensors relative to tags without. For example, a session that involves a host tag stopping in proximity to a neighbor tag carries a higher risk of transmitting an infectious agent than a session that involves tag hosts passing at a constant velocity. Constant-velocity passing would suggests a person walking past a neighbor with reduced interaction, such as two people passing in a hallway or a person passing an open doorway. Stopping would suggest a more interactive event, such as providing care to a patient (for a health-care worker as host and patient as neighbor) or hand sanitizing (if the neighbor tag is a hand sanitizer or wash basin). Such tags could record the event as a discrete parameter, or they could add or subtract a numeric adjustment to a Profile Risk Value, such by adding or subtracting a fixed amount for each stop. Alternately tags could make a time-weighted and/or range-weighted adjustment for stops. Further still, tags could adjust the risk factor downward as a function of velocity. Further still, tags could adjust risk factor based on measured extremity activity. Higher amplitude measurements of wrist or arm motion could signify higher risk activity, such as providing hands-on patient care, while lower amplitude measurements of wrist or arm motion could signify lower risk activity, such as talking with arms stationary.

The methods and systems also can initiate event-specific notifications based on motion sensing. For example, many hospital protocols call for care providers (such as doctors and nurses) to sanitize their hands between patient contacts. Tags with motion sensing can detect patterns of movement associated with a patient interaction, such as having stopped for periods of time at a close range to a patient. Tags also can detect patterns of movement associated with hand sanitizing, such as stopping at a hand sanitizer or wash basin. The absence of sanitizing events when in range of a sanitizing site indicates a failure to sanitize. Tags (or other elements of a system with access to the database) can monitor for a sequence of events consisting of two patient-care sessions without an intervening hand sanitizing session. Such an event could trigger a notification to the health-care worker of a possible breech in protocol, such as by sending a text message to the worker. Alternately, tags (or other elements of a system) could detect a sequence consisting of a patient-care session followed by an event where the health-care worker passed a hand-sanitizing station without stopping to sanitize. Tags (or other elements of a system) could send a text message to the worker reminding him/her to sanitize promptly. Alternately, or in addition, tags can record such events for analysis later when an infection control professional conducts a proximity trace and makes a decision to intervene with a tag bearer.

Figure 16:
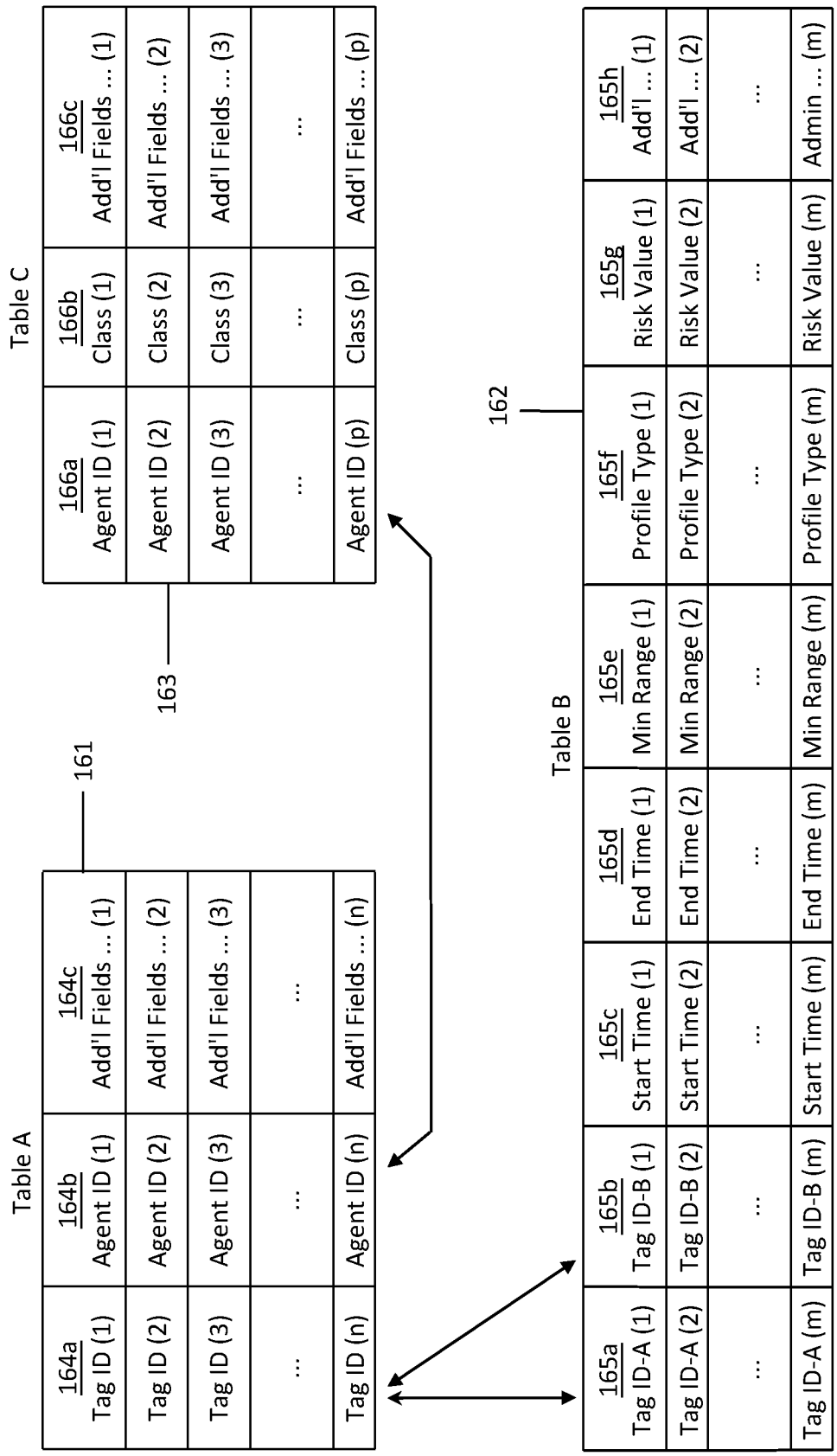
FIG. 16 illustrates a field structure for a database of proximity-event information.

FIG. 16 illustrates a database structure suitable for proximity-tracing methods and systems. FIG. 16 shows three database tables: Table A 161, Table B 162, and Table C 163. This architecture utilizes a relational database in which tables are associated by common fields, though non-relational databases also may be used.

Table A 161 includes a record (illustrated as a row) for each tag in a system. Fields of each record (illustrated as columns) include, by way of example: a unique identifier for each tag 164a, an identity of an agent bearing the tag 164b, and additional information 164c, which may be useful for administration and other purposes. Tag identification information may be, for example, a device serial number, a manufacturer-assigned Media Access Control (MAC) address, a manufacturer-assigned Bluetooth address, or other identifier. An "agent" in Table A may be any entity associated with the tag, such as a patient, health-care worker, serial number of a piece of equipment to which a tag may be attached (such as hospital bed, crash cart, etc.), or site identifier (e.g., nursing station, supply room, etc.). Other administrative information may include, for example, a date when the tag was put into service, a type of tag if different hardware is used (e.g., for mobile and fixed-site assignments), etc.

Table B 162 includes a record (illustrated as a row) for each reported proximity event. Fields of each record (illustrated as columns) include, by way of example: a unique identifier 165a for a first tag involved in the proximity event, a unique identifier 165b for a second tag involved in the proximity event, a start time 165c of the proximity event, an end time 165d of the proximity event, a minimum range 165e detected during proximity event, one or more profile types 165f for the event, and one or more risk values 165g for the event. An additional field may be included for a duration of a proximity event, or duration could be substituted for proximity event end time 165d. Fields for tag IDs 165a, 165b of Table B 162 link to fields for tag IDs 164a of Table A 161, thereby forming relationships among information in the two tables. Profile types 165f will be of the same types as used in the tags and may be generic (e.g., touch contact or airborne transmission) or more specific (e.g., influenza-like diseases or even specific diseases such as tuberculosis or Ebola). A record may include additional fields 165h, such as for a unique identifier for each event.

Table C 163 includes a record (illustrated as a row) for each agent of the system. Fields of each record (illustrated as columns) include, by way of example, an agent identifier 166a, and a class 166b. Table C 163 may include additional information 166c about each agent, such as for administrative or other purposes. Fields for Agent IDs 166a of Table C 163 link to fields of Agent IDs 164b of Table A 161, thereby forming relationships among information in the two tables.

Reports from the system may be adapted to assist infection control officials. A simple report would list all proximity events for an index case (person or fomite) over a relevant time period for a relevant risk profile, including risk values for the profile. Preferably, the report would order the records with high-risk proximity events first and lower-risk proximity events last. Alternately, the report would order the records with the agent (person or fomite) having the highest cumulative risk first and the lowest cumulative risk last. That is, for each agent pair (index agent and contactee), the report would list first those contactees for whom the sum of risk values for relevant proximity events is the highest. Other agents would be listed in order of their respective risk-value sums. For example, a first contactee might have a single proximity event with a risk value of eight (8), while a second contact might have 10 proximity events whose risk values add to a value of 50. A report would list the second contactee first, and the first contactee second. With this information, an infection control official could allocate resources more efficiently, such as by intervening with the highest-risk contactee first, selecting less expensive interventions for lower-risk contactees, and not intervening at all for contactees having cumulative risk values below a cutoff value.

A variety of data processing capabilities may be placed optionally in different system locations, such as tags or servers. For example, tags may record locally their session start and end times and report only start time and end times to the database. Computation of contact duration may be done at the server when it receives a new contact record. Alternately, tags might compute duration and report all three values (start time, end time, and duration). In addition, new proximity events may be evaluated for various conditions of merit at different locations. For example, the arrival of information at the server of a proximity event between a health-care worker and a patient could trigger an automatic search of the database for that health-care worker's prior-reported proximity events with patients and sanitizing stations. If the database does not show an adequate hand-sanitizing contact (such as a failure to stop), the health-care worker might not have practiced optimum infection control protocol, and the server could adjust risk factors of subsequent proximity events, such as by adding a factor to Risk Profile Values or by making an entry in an additional database field. Alternately, a tag may consult a local store of proximity events and make adjustments locally.

The hardware host for the database is not critical and may be selected according to cost, expected load, and other considerations. Potential platforms could include, for example, mainframes, server farms, individual or redundant servers, desktop computers and laptop computers. An exemplary platform for a relatively low-load implementation could be a desktop- or laptop-type computer based on an Intel™, multi-core i5 or i7 processor.

An exemplary software architecture could implement the database as part of a so-called LAMP-model web service stack, though so-called WAMP or other architectures and service models may be used. A LAMP stack typically includes: a Unix-like operating system (such as Ubuntu, Debian, or other Linux operating system), a web server (such as Apache, Cherokee or other server), a database (such as MY SQL, Mongo, object-oriented, or other database), and a user interface with scripting language (such as PHP, Python, Java or other). An exemplary user interface may include PHPMYADMIN or other interface. Most of these are open source and may be adapted to provide novel aspects as described above. It is expected that available host platforms will evolve over time, and future hardware platforms, software architectures, and database instantiations may be used.

The embodiments described above are intended to be illustrative but not limiting. Various modifications may be made without departing from the scope of the invention.

What is claim is:

1. An infection control method for multiple classes of pathogens, where a first class of pathogens is characterized by transmission across a first range by a first transmission mode, and a second class of pathogens is characterized by transmission across ranges greater than the first range by a second transmission mode different from the first transmission mode, said infection control method comprising steps of:
   (a) associating a proximity-detection device with each agent in a population of agents, where proximity-detection devices are capable of being detected by other devices, and where agents are selected from a set of people, sites, and apparatus;
   (b) detecting proximity events between pairs of agents using proximity-detection devices;
   (c) for each proximity event, measuring,
      (i) a first profile risk value for a first class of pathogens proportional to a first sum of time intervals $\Delta t/f_1(r)$, where $f_1(r)$ is a weighting function giving increased weights for closer measured ranges between proximity-detection devices, and
      (ii) a second profile risk value for a second class of pathogens proportional to a second sum of time intervals $\Delta t/f_2(r)$, where $f_2(r)$ is a weighting function giving increased weights for closer measured ranges between proximity-detection devices;
   (d) recording the profile risk values for proximity events;
   (e) at a time after recording the profile risk values, selecting criteria for an infection control intervention where the criteria include,
      (i) selecting a class of pathogen, and
      (ii) selecting a first index agent from the population of agents;
   (f) selecting a subpopulation of agents from the population of agents for intervention to include agents in the population of agents having recorded profile risk values for the selected class of pathogen with the first index agent during a first time interval; and
   (g) conducting an infection control intervention on the subpopulation of agents, where the infection control intervention is selected from the set of:
      (i) vaccinating a person in the subpopulation of agents, and
      (ii) disinfecting an agent.

2. A correlative method as in claim 1 wherein:
   (a) the step of selecting criteria for an infection control intervention further includes a step of selecting a second index agent from the population of agents; and
   (b) the step of selecting a subpopulation of agents includes agents who,
      (i) have recorded profile risk values for the selected pathogen with the first index agent in the first time interval, and
      (ii) have recorded profile risk values for the selected pathogen with the second index agent in a second time interval.

3. A method as in claim 1 wherein a weighting function varies linearly with a range r, wherein the range r is a range between proximity-detection devices.

4. A method as in claim 1 wherein a weighting function varies according to a square of the range r.

5. A method as in claim 1 wherein a weighting function gives zero weight to ranges greater than a predetermined value of the range r.

6. A method as in claim 1 wherein a class of pathogens is characterized by transmission by touch contact.

7. A method as in claim 1 wherein a class of pathogens is characterized by transmission by cough droplet.

8. A method as in claim 1 wherein an agent in the population of agents is a hand sanitizer.

9. A method as in claim 1 wherein an agent in the population of agents is a sink.

10. A method as in claim 1 wherein an agent in the population of agents is a fomite.

11. A method as in claim 10 wherein the fomite is mobile.

12. A method as in claim 10 wherein a proximity-detection device associated with the fomite is capable of detecting proximity with a proximity-detection device associated with a person.

* * * * *